United States Patent
Miyashita

(10) Patent No.: US 8,251,905 B2
(45) Date of Patent: Aug. 28, 2012

(54) BLOOD GLUCOSE MEASURING DEVICE AND METHOD OF MEASURING AVERAGE POSTPRANDIAL BLOOD GLUCOSE

(75) Inventor: Mariko Miyashita, Tokyo (JP)

(73) Assignee: Tanita Corporation, Itabashi-ku, Tokyo (JP)

( * ) Notice: Subject to any disclaimer, the term of this patent is extended or adjusted under 35 U.S.C. 154(b) by 625 days.

(21) Appl. No.: 12/405,653

(22) Filed: Mar. 17, 2009

(65) Prior Publication Data

US 2009/0292190 A1   Nov. 26, 2009

(30) Foreign Application Priority Data

May 22, 2008   (JP) ................................. 2008-134584

(51) Int. Cl.
   *A61B 5/00*   (2006.01)
(52) U.S. Cl. .................. 600/365; 702/19; 204/403.01; 204/403.1; 422/50; 422/52; 422/400; 422/82.01; 422/82.09; 205/777.5; 205/778; 205/792
(58) Field of Classification Search .......... 600/365; 702/19; 422/52, 400, 402, 82.01–82.09, 422/50; 205/777.5, 778, 792; 204/403.01–403.1
   See application file for complete search history.

(56) References Cited

U.S. PATENT DOCUMENTS

| | | | | |
|---|---|---|---|---|
| 4,962,550 | A | * | 10/1990 | Ikenaga et al. ............... 4/420 |
| 5,772,606 | A | * | 6/1998 | Ashibe et al. ............... 600/573 |
| 5,876,952 | A | * | 3/1999 | Shieh ....................... 435/14 |
| 6,021,339 | A | * | 2/2000 | Saito et al. ................ 600/345 |
| 6,198,954 | B1 | * | 3/2001 | Saito et al. ................ 600/345 |
| 6,444,169 | B1 | * | 9/2002 | Evtodienko et al. ......... 422/420 |
| D585,992 | S | * | 2/2009 | Kousuge ................... D24/186 |

(Continued)

FOREIGN PATENT DOCUMENTS

| | | | |
|---|---|---|---|
| JP | 2001153871 A | * | 6/2001 |
| JP | 2003-270241 A | | 9/2003 |
| JP | 2004-286452 A | | 10/2004 |

OTHER PUBLICATIONS

Non-invasive monitoring of gingival crevicular fluid for estimation of blood glucose level, M. Yamaguchi, Y. Kawabata, S. Kambe, K. Wardell, F. H. Nystrom, K. Naitoh and H. Yoshida, Medical and Biological Engineering and Computing, vol. 42, No. 3, 322-327, 2004.*

(Continued)

*Primary Examiner* — Navin Natnithithadha
*Assistant Examiner* — Sunita Reddy
(74) *Attorney, Agent, or Firm* — Buchanan Ingersoll & Rooney PC

(57) ABSTRACT

A practical measuring device and a measuring method that allow simply measuring average postprandial blood glucose from urinary glucose. The blood glucose measuring device includes a measuring unit that measures postprandial urinary glucose from subject's urine at a predetermined time after meal, a processing unit that calculates average postprandial blood glucose through a period up to the predetermined time after meal, based on the postprandial urinary glucose, a storage unit that stores calibration data including the postprandial urinary glucose and the average postprandial blood glucose in association, and an output unit that outputs data indicating the calculated average postprandial blood glucose. The processing unit calculates the average postprandial blood glucose, based on the postprandial urinary glucose from the urine of the subject who has intaken a desired amount of water or perspired in the period up to the predetermined time after meal, and the calibration data.

14 Claims, 18 Drawing Sheets

U.S. PATENT DOCUMENTS

| | | | |
|---|---|---|---|
| 7,727,769 B2* | 6/2010 | Fukuda | 436/149 |
| 2003/0022385 A1* | 1/2003 | Evtodienko et al. | 436/95 |
| 2003/0203499 A1* | 10/2003 | Evtodienko et al. | 436/95 |
| 2003/0208113 A1* | 11/2003 | Mault et al. | 600/316 |
| 2004/0185568 A1* | 9/2004 | Matsumoto | 436/8 |
| 2005/0234311 A1* | 10/2005 | Kouchi et al. | 600/300 |

OTHER PUBLICATIONS

Khaw KT, Wareham N, Bingham S, Luben R, Welch A, Day N: Association of hemoglobin A1c with cardiovascular disease and mortality in adults: the European Prospective Investigation into Cancer in Norfolk. Ann Intern Med 141:413-420, 2004.*

H.D. Park, K.J. Lee, H.R. Yoon and H.H. Nam, Design of a portable urine glucose monitoring system for health care, Comput Biol Med 35 (2005), pp. 275-286.*

Koch, The Role of Urine Glucose Testing in the Management of Diabetes Mellitus, Canadian Journal of Diabetes, 2004;28(3):238-245.*

The Japanese Journal of Clinical Medicine, Nippon Rinsho, vol. 60, Suppl. 8, 2002, p. 524-525.

* cited by examiner

MALE (HbA1c7.5-8.9)
AUC180 (n=19) R=0.82

$y = 0.0254x + 196.59$
$R^2 = 0.6684$

FEMALE (HbA1c7.5-8.9)
AUC180 (n=24) R=0.50

$y = 0.0249x + 218.91$
$R^2 = 0.2536$

BLOOD GLUCOSE MEASURING DEVICE AND METHOD OF MEASURING AVERAGE POSTPRANDIAL BLOOD GLUCOSE

This application is based on Japanese patent application No. 2008-134584, the content of which is incorporated hereinto by reference.

BACKGROUND

1. Field of the Invention

The present invention relates to a technique of measuring average postprandial blood glucose.

2. Related Art

Postprandial blood glucose measurement has lately come to be spotlighted as an important procedure in blood glucose control. As an index indicating the severity of diabetes the level of average postprandial blood glucose is popularly adopted, and measured data thereof is utilized to evaluate the sugar metabolism performance of a patient.

The postprandial blood glucose (instantaneous blood glucose) incessantly fluctuates with the lapse of time after meal, and hence the blood glucose measurement has conventionally been executed over a plurality of times at short intervals after meal, in order to calculate the average postprandial blood glucose. The calculation of the average postprandial blood glucose is obtained through drawing a curve representing the blood glucose fluctuation based on the instantaneous blood glucose, which is fluctuating time after time, calculating the Area of a region Under the Curve but upper than a predetermined renal glucose excretion threshold (hereinafter, AUC), and then calculating the time-based average of the AUC.

For individual patients, however, it is a burden to measure the instantaneous blood glucose over a plurality of times after every meal, and therefore a technique that allows diabetic patients and those who have high blood glucose levels to daily and simply check the average postprandial blood glucose has been eagerly sought for.

The solution conventionally attempted includes estimating the instantaneous blood glucose based on urinary glucose. To cite a few examples, JP-A No. 2003-270241 discloses a technique of estimating the instantaneous blood glucose of a subject at the time of the measurement, by storing in advance the long-term fluctuation pattern of the urinary glucose of the subject. Also, JP-A No. 2004-286452 teaches a method of estimating the instantaneous blood glucose based on the urinary glucose of the subject measured upon collecting the urine, by statistically analyzing in advance the relationship between the urinary glucose and the blood glucose with respect to each individual subject.

[Patent document 1] JP-A No. 2003-270241
[Patent document 2] JP-A No. 2004-286452
[Non-patent document 1] The Japanese Journal of Clinical Medicine, p. 524-525, Vol. 60, Special Edition No. 8, 2002 published by Nippon Rinsho Co., Ltd.

The measurement of the postprandial urinary glucose is easy and hence offers the advantage that the patient is exempted from the burden, compared with the direct measurement of the blood sugar concentration executed through collecting the blood. The urinary glucose is, however, prone to largely fluctuate in case that the urine is condensed or diluted by water intake or excretion by the patient (except urination), such as drinking water or perspiration, and hence it has been widely believed that it is technically difficult to accurately estimate the instantaneous blood glucose based on the urinary glucose (Ref. the non-patent document 1). In other words, the urinary glucose is an integral parameter determined by the amount of urine stored in the urinary bladder after the previous urination and the amount of urinary glucose contained therein, and therefore such parameter is considered to be inappropriate for estimating the instantaneous blood glucose, which fluctuates time after time.

The patent document 1 does not provide a specific method of estimating the instantaneous blood glucose based on the urinary glucose. Moreover, the procedure according to this literature requires accumulating the correlation between the urinary glucose and the instantaneous blood glucose of the subject over a long period of time and establishing the correlation as data in advance. This point constitutes a major drawback that the procedure is inapplicable to general patients whose long-term correlation data acquired as above is unavailable.

This is also the case with the patent document 2, which requires acquiring the statistical data in advance, with respect to each patient.

Meanwhile, since the conventional measurement of the average postprandial blood glucose requires establishing a time-serial fluctuation pattern of the instantaneous blood glucose fluctuating time after time, the calculation thereof based on the urinary glucose is not involved.

In the case of the method according to the patent document 2 for example, it is an excessive burden for the patient to collect a predetermined amount of urine at short intervals, such as every 15 minutes or every 30 minutes, after each meal. Besides, since a sufficient amount of urine is not always collectable, it is practically impossible to draw an accurate blood glucose curve to thereby calculate the AUC, despite the trouble of repeatedly measuring the urinary glucose and converting the value into the instantaneous blood glucose.

Consequently, it is impossible to acquire the average postprandial blood glucose based on the measured level of the urinary glucose, as long as depending on the fluctuation pattern of the instantaneous blood glucose as in the conventional methods, to calculate the average postprandial blood glucose. Thus, actually it has been the only way for acquiring the average postprandial blood glucose, to repeatedly measure the blood sugar concentration at short intervals.

The present invention has been accomplished in view of the foregoing problem, and provides a practical measuring device that allows a patient to simply measure the average postprandial blood glucose based on the urinary glucose, and a method of measuring the same.

SUMMARY

The present inventor has discovered that in the case where water intake/excretion takes place in a subject through drinking water or perspiration, the correlation between the urinary glucose and the average postprandial blood glucose is maintained despite the fluctuation in level of the urinary glucose and of the instantaneous blood glucose. This has led to the conclusion that the average postprandial blood glucose can be estimated based on the measurement of the urinary glucose at a predetermined time after meal (postprandial urinary glucose), irrespective of the water intake/excretion condition (hereinafter occasionally referred to as water intake condition) of the subject.

The present inventor has further discovered that acquiring calibration data showing the correlation between the postprandial urinary glucose and the average postprandial blood glucose from a multitude of sample providers and statistically analyzing the correlation in advance enables estimating the average postprandial blood glucose based on the calibration data thus acquired and the measurement data of the postprandial urinary glucose of the subject. Thus, the discovery by the present inventor that the water intake condition, which has so far been considered as a primary factor of the fluctuation in urinary glucose, actually does not affect the estimation of the blood glucose has led to proving the feasibility of the estimation of the average postprandial blood glucose of the subject, based on the calibration data established from the measurement data of the postprandial urinary glucose acquired from the sample providers.

The present inventor has then actually acquired the calibration data from numerous sample providers, to thereby further discover that a certain correlation lies between the postprandial urinary glucose and the average postprandial blood glucose.

The present invention has thus been accomplished, which provides a completely novel method of estimating the average postprandial blood glucose based on the postprandial urinary glucose, without the need to depend on the fluctuation pattern of the instantaneous blood glucose, which fluctuates with time after meal.

In one embodiment, there is provided a blood glucose measuring device, comprising:

a measuring unit that measures postprandial urinary glucose from urine of a subject at a predetermined time after meal;

a processing unit that calculates average postprandial blood glucose through a period up to the predetermined time after meal, based on the postprandial urinary glucose measured; and an output unit that outputs data indicating the average postprandial blood glucose calculated.

In a more specific embodiment of the blood glucose measuring device thus constructed, the measuring unit may accept the urine of the subject who has intaken water or perspired in the period up to the predetermined time after meal, to thereby measure the postprandial urinary glucose.

In a more specific embodiment, the blood glucose measuring device may further comprise a storage unit that stores calibration data including the postprandial urinary glucose and the average postprandial blood glucose as associated data; and the processing unit may calculate the average postprandial blood glucose based on the postprandial urinary glucose measured from the urine of the subject who has intaken water or perspired in the period up to the predetermined time after meal, and the postprandial urinary glucose measured from the urine of the subject who has neither intaken water nor perspired in the period up to the predetermined time after meal, utilizing the calibration data in common.

In a more specific embodiment, the blood glucose measuring device may further comprise an input unit that accepts an input of at least one of sex information indicating the sex of the subject, blood information indicating hemoglobin A1c concentration of the subject, and ratio information indicating a level of a conversion ratio from the postprandial urinary glucose to the average postprandial blood glucose of the subject; and the processing unit may calculate the average postprandial blood glucose based on the measured postprandial urinary glucose, and at least one of the sex information, the blood information and the ratio information.

In a more specific embodiment of the blood glucose measuring device, the input unit may accept an input of the ratio information selected from two types being high and low respectively.

In another embodiment, there is provided a method of measuring average postprandial blood glucose, comprising:

acquiring calibration data indicating a relationship between a postprandial urinary glucose at a predetermined time after meal and an average postprandial blood glucose, from a plurality of sample providers;

measuring the postprandial urinary glucose of a subject at the predetermined time after meal; and estimating the average postprandial blood glucose of the subject based on the postprandial urinary glucose measured and the calibration data.

In a more specific embodiment of the method thus arranged, the acquiring calibration data may include acquiring sample data from each of the sample providers indicating a correlation between the area of a region under a curve of a postprandial blood glucose but upper than a predetermined renal glucose excretion threshold and the postprandial urinary glucose, and statistically analyzing a plurality of sample data, to thereby calculate the calibration data.

In a more specific embodiment of the method thus arranged, the calibration data calculated through statistical analysis may form a calibration line defined by an equation (2):

$$\text{Average postprandial blood glucose} = \text{regression coefficient} \times \text{postprandial urinary glucose} + \text{threshold value} \quad (2)$$

In a more specific embodiment of the method thus arranged, the renal glucose excretion threshold may be adopted as the threshold value and the regression coefficient may be specified as $2 \times 10^{-2}$, in the case where the subject is a male and has a hemoglobin A1c concentration lower than 9.0%, and the renal glucose excretion threshold may be adopted as the threshold value and the regression coefficient may be specified as $3 \times 10^{-2}$, in the case where the subject is a female and has a hemoglobin A1c concentration lower than 7.5%.

In a more specific embodiment of the method thus arranged, in which the acquiring calibration data includes classifying the sample data acquired from the sample providers into a plurality of groups, and calculating the calibration data based on the sample data of the respective groups;

the method may further comprise acquiring the sample data of the subject in advance; and the estimating the average postprandial blood glucose may include identifying the group to which the sample data acquired of the subject belongs, and estimating the average postprandial blood glucose of the subject based on the calibration data corresponding to the group identified and the postprandial urinary glucose measured.

In a more specific embodiment of the method thus arranged, the sample providers and the subject may include a male having a hemoglobin A1c concentration lower than 9.0%.

It is to be noted that in the present invention the average postprandial blood glucose through the period up to the predetermined time after meal may be calculated with respect to the entirety of such period, or to a part of that period. In the latter case, it is preferable that the period includes a time zone in which glucose is predominantly excreted into the urine of the subject.

Each constituent of the blood glucose measuring device according to the present invention has only to be capable of performing its function, and may be constituted in a form of, for example, an exclusive hardware that performs a predetermined function, a data processor in which a predetermined function is incorporated as a computer program, a predetermined function realized in a data processor by a computer program, and an optional combination thereof. Also, the blood glucose measuring device according to the present invention may be embodied in a form of a hardware constructed of general-purpose devices such as a Central Processing Unit (CPU), a Read Only Memory (ROM), a Random Access Memory (RAM), and an Interface (I/F) unit, exclusive logic circuits designed to execute predetermined data processing, and an appropriate combination thereof, so as to read out a computer program and thereby execute the corresponding data processing.

It is to be noted that the constituents of the present invention do not necessarily have to be individually independent, but may be configured such that a plurality of constituents constitutes a single member, that a constituent is composed of a plurality of members, that a constituent is a part of another constituent, that a part of a constituent and a part of another constituent overlap, and so forth.

Although a plurality of steps may be sequentially stated in the description of the measurement method of average postprandial blood glucose according to the present invention, such sequence does not necessarily limit the order in practically executing those steps, unless so expressed.

Further, the plurality of steps does not have to be individually executed at different timings unless so expressed, but may be arranged such that one of the steps is executed during the execution of another, that the execution timing of a step partially or entirely overlap that of another, and so forth.

The blood glucose measuring device and the method of measuring the average postprandial blood glucose according to the present invention exempt the subject from acquiring in advance a large amount of calibration data indicating the correlation between his/her postprandial urinary glucose and average postprandial blood glucose. Such arrangement enables the subject to easily check the average postprandial blood glucose thus to obtain the index indicating the severity of diabetes, simply by collecting the urine once at a predetermined time after meal and thereby measuring the urinary glucose.

BRIEF DESCRIPTION OF THE DRAWINGS

The above and other objects, advantages and features of the present invention will be more apparent from the following description taken in conjunction with the accompanying drawings, in which.

DETAILED DESCRIPTION

The present invention will be now described herein with reference to illustrative embodiments. Those skilled in the art will recognize that many alternative embodiments can be accomplished using the teachings of the present invention and that the invention is not limited to the embodiments illustrated for explanatory purposes.

Figure 1:
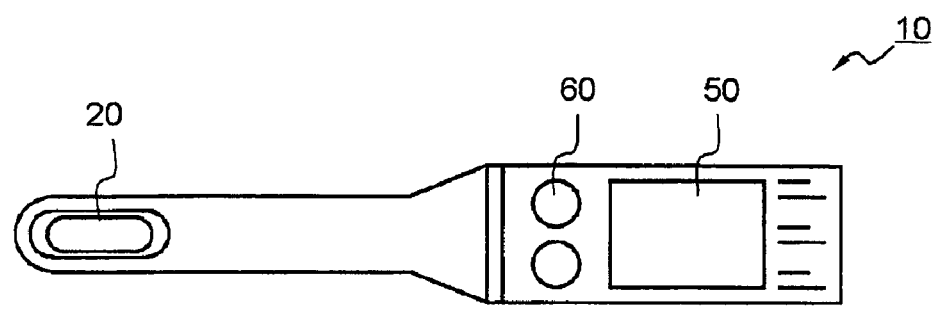
FIG. 1 is a plan view showing an appearance of a blood glucose measuring device according to an embodiment of the present invention.
Figure 2:
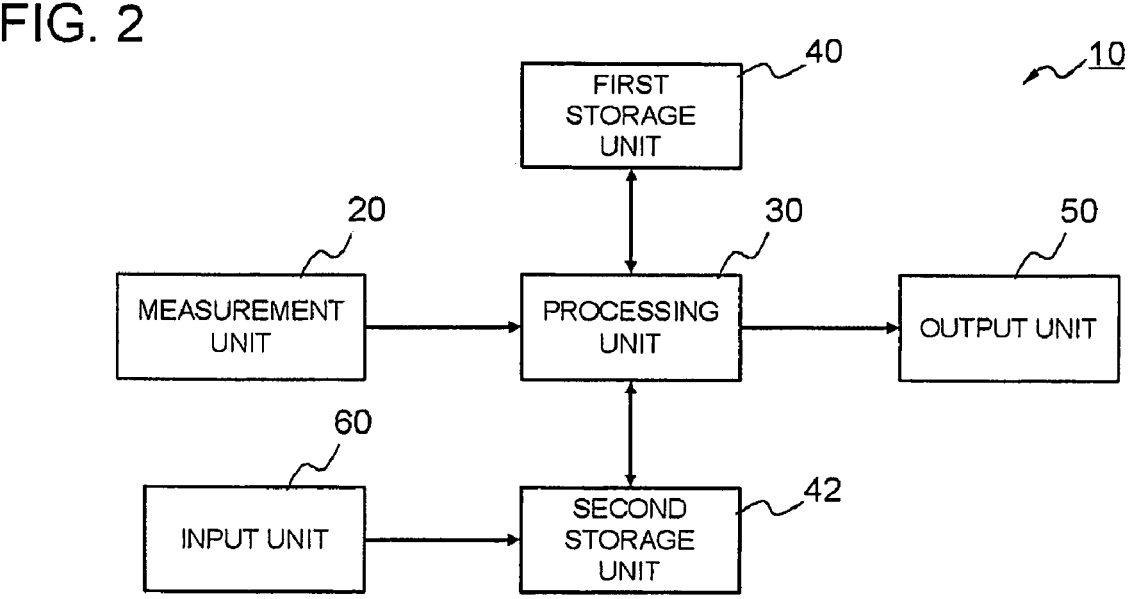
FIG. 2 is a block diagram showing a configuration of the blood glucose measuring device according to the embodiment.

Hereunder, a blood glucose measuring device (hereinafter occasionally abbreviated as measuring device) and a method of measuring average postprandial blood glucose (hereinafter occasionally abbreviated as measurement method) according to an embodiment of the present invention will be described in details, referring to the drawings. In all the drawings, same or similar constituents are given the same numeral, and the description thereof will not be repeated. FIG. 1 is a plan view showing an appearance of a blood glucose measuring device according to the embodiment, and FIG. 2 is a block diagram showing a configuration thereof.

[Blood Glucose Measuring Device]

First, the outline of the blood glucose measuring device according to this embodiment will be described.

The blood glucose measuring device 10 includes a measuring unit 20 that measures a postprandial urinary glucose from urine of a subject at a predetermined time after meal, a processing unit 30 that calculates an average postprandial blood glucose based on the measured postprandial urinary glucose, and an output unit 50 that outputs data indicating the calculated average postprandial blood glucose.

In the blood glucose measuring device 10, the measuring unit 20 can also accept urine of a subject who has intaken water or perspired in the period up to the predetermined time after meal, and measure the postprandial urinary glucose of such subject.

The blood glucose measuring device 10 further includes a storage unit (first storage unit 40) that stores therein calibration data of the postprandial urinary glucose and the average postprandial blood glucose associated therewith.

The processing unit 30 utilizes the calibration data in common with respect to the subject who has intaken water or perspired in the period up to the predetermined time after meal and the subject who has neither intaken water nor perspired in the same period, when calculating the average postprandial blood glucose based on the postprandial urinary glucose measured from the urine.

In other words, the processing unit 30 according to this embodiment calculates the average postprandial blood glucose based on the same calibration data, irrespective of the water intake condition of the subject.

The measuring unit 20 includes a urinary glucose sensor to be soaked in the urine collected from the subject, to thereby electrochemically detect sugar content in the urine. The urinary glucose sensor measures the urinary glucose in the urine, and outputs a urinary glucose signal indicating the level thereof, to the processing unit 30.

The calibration data stored in the first storage unit 40 indicates the correlation between the postprandial urinary glucose at the predetermined time after meal and the average postprandial blood glucose. Such calibration data is acquired from a plurality of sample providers, and input to the first storage unit 40.

The calibration data may be statistical data that directly associates the two parameters, the postprandial urinary glucose and the average postprandial blood glucose, or that associates other parameters which are convertible from the former parameters.

Although the number of sample providers is not specifically determined, it is desirable to acquire the sample from at least 10 persons, preferably from 20 persons or more, and more preferably from 100 persons or more, in order to secure sufficient credibility of the calibration data.

To acquire the calibration data, it is preferable to have the sample providers undergo a meal load testing, and to measure the urinary glucose at a predetermined time after meal. The elapsed time after meal may be appropriately selected from 90 minutes, 120 minutes, 150 minutes, or 180 minutes. It is preferable that the elapsed time (predetermined time) is of such a length that does not impose an excessive burden on the sample providers, who are restricted from urinating during that period. Also, it is preferable that the elapsed time is long enough for the instantaneous blood glucose, which reaches a peak after meal, to return to a normal level. Collecting the urine at the time when the instantaneous blood glucose has sufficiently decreased assures that the collected urine contains substantially the entire amount of the glucose that has exceeded the renal glucose excretion threshold, and thus been excreted into the blood. Such procedure enables improving the accuracy of measurement of the postprandial urinary glucose and the average postprandial blood glucose.

The calibration data can be calculated based on the fact that the AUC of the postprandial blood glucose upper than the predetermined renal glucose excretion threshold and the average postprandial blood glucose are convertible. More specifically, acquiring from each sample provider the sample data indicating the correlation between the AUC and the postprandial urinary glucose, and statistically analyzing the acquired sample data leads to establishing a relationship between the postprandial urinary glucose and the average postprandial blood glucose.

The calculating method and pattern of the calibration data are not specifically determined. For example, the relationship between the postprandial urinary glucose and the AUC of the postprandial blood glucose, or the average postprandial blood glucose, may be approximated through a first-order function based on the minimum square method. Alternatively, the calibration data may be set up by associating the postprandial urinary glucose and the average postprandial blood glucose, through a multi-order function, an exponential function, a logarithmic function, or a combination thereof.

The calibration data may be stored in the first storage unit 40 in a form of a function as in this embodiment, or in a form of a lookup table.

The blood glucose measuring device 10 according to this embodiment estimates the average postprandial blood glucose of a subject based on his/her postprandial urinary glucose, utilizing the calibration data acquired from a multitude of people.

It is preferable to have the subject also undergo the meal load testing like the sample providers, and collect the urine for measuring the postprandial urinary glucose of the subject at the predetermined time after meal. Here, the meal for the subject may be prepared as a meal for load testing as with the sample providers, or may be an ordinary meal.

When measuring the average postprandial blood glucose of the subject with the blood glucose measuring device 10 according to this embodiment, the subject is permitted to drink water or perspire as desired, during and after meal. In other words, the blood glucose measuring device 10 according to this embodiment is capable of measuring the average postprandial blood glucose of the subject, without the need to strictly control the amount of water intaken by the subject with the meal.

The calibration data stored in the first storage unit 40 according to this embodiment may be the data that associates the postprandial urinary glucose and the average postprandial blood glucose of all the sample providers. Alternatively, the sample providers may be classified into a plurality of categories from various viewpoints, to thereby build up correlation data of the postprandial urinary glucose and the average postprandial blood glucose of the sample providers of the respective categories, as the calibration data.

Specifically, the blood glucose measuring device 10 according to this embodiment stores the calibration data with respect to the categories classified based on sex and level of hemoglobin A1c (HbA1c) concentration.

With the blood glucose measuring device 10, the subject can operate an input unit 60 to thereby select the category to which the subject belongs, before or after soaking the measuring unit 20 in the urine for measuring the urinary glucose.

In this embodiment, a plurality of groups indicating the level of the average postprandial blood glucose with respect to the postprandial urinary glucose (conversion ratio) is also provided, as the classified categories.

Thus, blood glucose measuring device 10 according to this embodiment further includes the input unit 60 that accepts an input of at least one of sex information indicating the sex of the subject, blood information indicating HbA1c concentration of the subject, and ratio information indicating the level of the conversion ratio from the postprandial urinary glucose to the average postprandial blood glucose of the subject.

The processing unit 30 calculates the average postprandial blood glucose based on the measured postprandial urinary glucose, and one of the sex information, the blood information and the ratio information that has been input.

The input unit 60 may be constituted of one or a plurality of buttons, and thereby accept the input of the sex selected from male and female, the HbA1c concentration selected from a plurality of classifications, as well as the ratio information selected from high and low.

The information input through the input unit 60 is stored in a second storage unit 42.

The processing unit 30 retrieves from the first storage unit 40 the calibration data corresponding to the category designated by the information stored in the second storage unit 42.

The processing unit 30 then applies the data of the postprandial urinary glucose, provided from the measuring unit 20, to the retrieved calibration data to thereby calculate the data of the average postprandial blood glucose of the subject.

The data thus calculated is output through the output unit 50, for the subject to recognize.

Although the output unit 50 is exemplified by a digital display unit in FIG. 1, the output unit 50 may be an external interface that outputs the data to an external storage device.

The blood glucose measuring device 10 according to this embodiment is designed to measure the urinary glucose in the urine collected at a predetermined time after meal, and is hence capable of practically measuring the average postprandial blood glucose with high accuracy, irrespective of the water intake condition of the subject. In particular, classifying the subjects into various categories and applying the suitable calibration data as in this embodiment further upgrades the measurement accuracy of the average postprandial blood glucose.

[Method of Measuring Blood Glucose]

Hereunder, general description will be given on a method of measuring the average postprandial blood glucose, to be executed with the blood glucose measuring device 10 according to this embodiment.

The method of measuring the average postprandial blood glucose according to this embodiment includes a sample acquisition process (step) including acquiring the calibration data indicating a relationship between the postprandial urinary glucose at a predetermined time after meal and the average postprandial blood glucose, from a plurality of sample providers. The measurement method according to this embodiment further includes a measurement process (step) including measuring the postprandial urinary glucose of a subject at the predetermined time after meal, and an estimation process (step) including estimating the average postprandial blood glucose of the subject based on the measured postprandial urinary glucose and the calibration data.

The measurement method according to this embodiment will now be described in details.

[Sample Acquisition Process]

In the sample acquisition process, the sample data indicating a correlation between the AUC of the postprandial blood glucose upper than a predetermined renal glucose excretion threshold and the postprandial urinary glucose is first acquired from each of the sample providers. Then the plurality of acquired sample data is statistically analyzed, to thereby calculate the calibration data.

The sample providers are each subjected to a meal load testing. It is preferable that all the sample providers keep the same water intake condition resultant from water intake or perspiration during and after such meal.

The sample providers are categorized by sex and the level of hemoglobin A1c (HbA1c) concentration. Then the sample data of each category is statistically analyzed, to thereby calculate the calibration data indicating the correlation between the postprandial urinary glucose and the average postprandial blood glucose.

The relationship between the postprandial urinary glucose and the average postprandial blood glucose can be obtained as follows.

Figure 3:
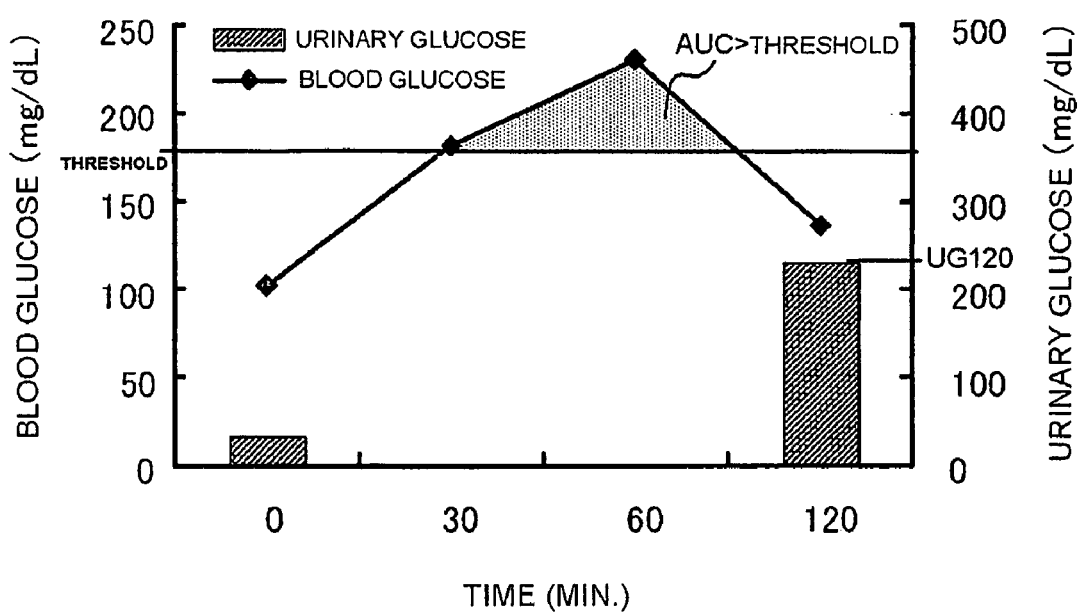
FIG. 3 is a graph for explaining a calculation method of AUC.

FIG. 3 is a graph showing a relationship between a measurement result indicating the fluctuation with time of the postprandial blood glucose (instantaneous blood glucose) and an AUC calculated from a renal glucose excretion threshold set at a predetermined level such as 180 mg/dL (AUC>180). The AUC can be converted into the average postprandial blood glucose through the following equation (3) which employs the elapsed time after meal and the renal glucose excretion threshold:

$$\text{Average postprandial blood glucose} = \text{renal glucose excretion threshold} + AUC/\text{elapsed time after meal} \quad (3)$$

Alternatively, the average postprandial blood glucose may be calculated from a partial time zone out of the elapsed time after meal.

In this case, the subject is to once urinate at the start of the partial time zone, and then the urine of the subject is collected at the end of the partial time zone for measuring the urinary glucose, to thereby calculate the AUC. Thus, the average blood glucose can be calculated with the equation (3) above, by substituting the elapsed time after meal with the length of the partial time zone (elapsed time).

In other words, the average postprandial blood glucose of the sample providers and the subject may be calculated with the following equation (3a), in this embodiment:

$$\text{Average postprandial blood glucose} = \text{renal glucose excretion threshold} + AUC/\text{elapsed time} \quad (3a)$$

In this embodiment, the urinary glucose measured from the urine collected at 120 minutes after meal (120-minutes urinary glucose) will be employed as the postprandial urinary glucose.

FIG. 3 also includes an example of the 120-minutes urinary glucose measured from urine collected at 120 minutes after meal, from a subject who urinated at 0 minute and 120 minutes after meal.

Thus, the calibration data indicating the correlation between the postprandial urinary glucose (120-minutes urinary glucose) and the average postprandial blood glucose of a sample provider can be obtained as shown in FIG. 3.

Then the sample data acquired from a multitude of sample providers is statistically analyzed to thereby obtain the calibration data. The calibration data may be obtained, for example, in a form of a calibration line represented by the following equation (4):

$$\text{Average postprandial blood glucose } (y) = \text{regression coefficient} \times \text{postprandial urinary glucose } (x) + \text{threshold value} \quad (4)$$

By the measurement method according to this embodiment, the sample providers may be categorized as below for example, to thereby calculate the calibration data with respect to each category.

In the case where the subject is a male having a HbA1c concentration lower than 9.0%, the average postprandial blood glucose (mg/dL) can be estimated through the following equation (5):

$$\text{Average postprandial blood glucose} = 2 \cdot 10^{-2} \times \text{postprandial urinary glucose} + \text{renal glucose excretion threshold} \quad (5)$$

Likewise, in the case where the subject is a female having a HbA1c concentration lower than 7.5%, the average postprandial blood glucose (mg/dL) can be estimated through the following equation (6):

$$\text{Average postprandial blood glucose} = 3 \cdot 10^{-2} \times \text{postprandial urinary glucose} + \text{renal glucose excretion threshold} \quad (6)$$

[Measurement Process]

The measurement method according to this embodiment includes measuring the postprandial urinary glucose of the subject at a predetermined time after meal. The predetermined time after meal for collecting the urine is to be the same as the elapsed time after meal in the case of acquiring the calibration data from the sample providers. In this embodiment, accordingly, the urinary glucose is measured at 120 minutes after meal (120-minutes urinary glucose), also with respect to the subject.

[Estimation Process]

By the measurement method according to this embodiment, the postprandial urinary glucose measured from the subject is then converted into the average postprandial blood glucose, utilizing the calibration data represented, for example, by the foregoing equations (4) to (6).

Once the subject recognizes such converted value, the subject can find out the severity of his/her diabetes.

The measurement method according to this embodiment thus enables estimating the average postprandial blood glucose of the subject utilizing the calibration data acquired from a multitude of sample providers. This is because it has been confirmed that high correlation lies between the postprandial urinary glucose and the average postprandial blood glucose, irrespective of the water intake condition which is normally different in many ways among the subjects.

Further, in this embodiment, the sample providers are classified into categories that exhibit higher correlation coefficient between the postprandial urinary glucose and the average postprandial blood glucose, for acquiring the calibration data. Reflecting thus the categorization of the subject enables upgrading the accuracy of the estimation of the average postprandial blood glucose, from the postprandial urinary glucose of that subject.

It is to be noted that various modifications may be made with respect to this embodiment.

For example, the sample providers may be categorized into a plurality of groups based on the conversion ratio, which indicates the level of the average postprandial blood glucose with respect to the postprandial urinary glucose, to thereby calculate the calibration data indicating the correlation between the postprandial urinary glucose and the average postprandial blood glucose, from the respective groups.

To be more detailed, as will be described in the subsequent working examples, a group having a relatively high average postprandial blood glucose and another group having a relatively low average postprandial blood glucose may be formed with respect to the same postprandial urinary glucose level, depending on how the sample providers are categorized. In this case, specifying in advance to which of such groups the subject belongs enables measuring the average postprandial blood glucose with higher accuracy in the subsequent measuring, based on the calibration data corresponding to the group to which the subject belongs.

To decide the group to which the subject is supposed to belong, in this modification, a commercially available blood glucose self tester is employed to measure the postprandial blood glucose to thereby calculate the average postprandial blood glucose, and also a commercially available digital urinary glucose meter is employed to measure the postprandial urinary glucose. Then upon associating those values it can be found out to which group the subject belongs. It suffices that the subject undergoes such procedure just once.

Thus, in the sample acquisition process according to this modification, the sample data acquired from the sample providers is classified into a plurality of groups, and the calibration data is calculated from the sample data that belongs to the respective groups.

Then a preparatory process follows, in which the sample data of the subject is acquired.

Further in the estimation process, the group to which the sample data of the subject acquired in the preparatory process is decided, and the average postprandial blood glucose of the subject is estimated based on the calibration data corresponding to the group thus decided and the postprandial urinary glucose measured in the measurement process.

Although the cause of the presence of a plurality of groups having different conversion ratios of the average postprandial blood glucose with respect to the same postprandial urinary glucose level has not been completely elucidated, a presumable reason is that the sample providers and the subjects include those who reach the maximal postprandial blood glucose level in approx. 60 minutes and approx. 120 minutes, depending on the insulin secretion function.

With the blood glucose measuring device 10 according to this embodiment, the calibration data of the postprandial urinary glucose and the average postprandial blood glucose a plurality of times after meal from the sample providers.

For example, the first storage unit 40 of the blood glucose measuring device 10 may store the calibration data based on the elapsed time after meal of 90 minutes, the calibration data based on the elapsed time of 120 minutes, and the calibration data based on the elapsed time of 150 minutes.

In this case, when the subject is to undergo the average postprandial blood glucose measurement, one of the calibration data corresponding to 90 minutes, 120 minutes and 150 minutes may be selected, depending on the elapsed time before the urine collection.

More specifically, the elapsed time after meal is selectively input through the input unit 60, before or after the measurement of the postprandial urinary glucose of the subject. The processing unit 30 then retrieves from the first storage unit 40 the calibration data corresponding to the elapsed time after meal that has been input, and applies the measurement result of the postprandial urinary glucose to the calibration data to thereby execute the calculation.

Such arrangement allows measuring the average postprandial urinary glucose without imposing excessive restriction of urination, on the subject. Also, in the case of a subject whose postprandial blood glucose quickly fluctuates, the measurement of the average postprandial urinary glucose can be executed at a relatively short elapsed time after meal.

WORKING EXAMPLES

The method of measuring the average postprandial blood glucose according to the present invention will now be described in further details, based on the following working examples.

Working Example 1

The present inventor measured the blood glucose and the urinary glucose, under different water intake conditions during and after the meal load testing.

Conditions of the experiment are as indicated in Table 1. The experiment was executed with respect to a person with impaired glucose tolerance (56-year-old male, hemoglobin A1c concentration: 5.6%). The procedure of the experiment was executing the meal loading with respect to one and the same subject, to thereby measure the correlation between the blood glucose and the urinary glucose under different water intake conditions during and after the meal loading.

TABLE 1

| | ELAPSED TIME AFTER MEAL [MIN.] | | | | | | | | | | | | |
|---|---|---|---|---|---|---|---|---|---|---|---|---|---|
| | 0 | 15 | 30 | 45 | 60 | 75 | 90 | 105 | 120 | 135 | 150 | 165 | 180 |
| Case 1 | | | | | | | | | | | | | |
| WATER INTAKEN [ml] | 100 | | | | | | | | | | | | |
| URINARY GLUCOSE MEASUREMENT | ● | | | | ● | | | | ● | | | | ● |
| BLOOD GLUCOSE MEASUREMENT | ● | ● | ● | ● | ● | ● | ● | ● | ● | ● | ● | ● | ● |
| Case 2 | | | | | | | | | | | | | |
| WATER INTAKEN [ml] | 200 | | 200 | | 200 | | 200 | | 200 | | 200 | | |
| URINARY GLUCOSE MEASUREMENT | ● | | | | ● | | | | ● | | | | ● |
| BLOOD GLUCOSE MEASUREMENT | ● | ● | ● | ● | ● | ● | ● | ● | ● | ● | ● | ● | ● |

In the Case 1, the subject intook 100 ml of water at the start of the meal load testing, i.e. immediately after meal.

In the Case 2, the subject intook 200 ml of water at the start of the meal load testing, i.e. immediately after meal, and 200 ml each every 30 minutes thereafter.

In both Cases 1 and 2, the blood glucose was measured immediately after meal and every 15 minutes thereafter. Also, the urinary glucose was measured immediately after meal and every 60 minutes thereafter. Such timings of the measurement are indicated by solid circles in the Table 1.

For the measurement, a commercially available blood glucose self tester operated by an electrode method, and a commercially available digital urinary glucose meter (for example, model UG-102 from Tanita Corporation) were employed.

Figure 4:
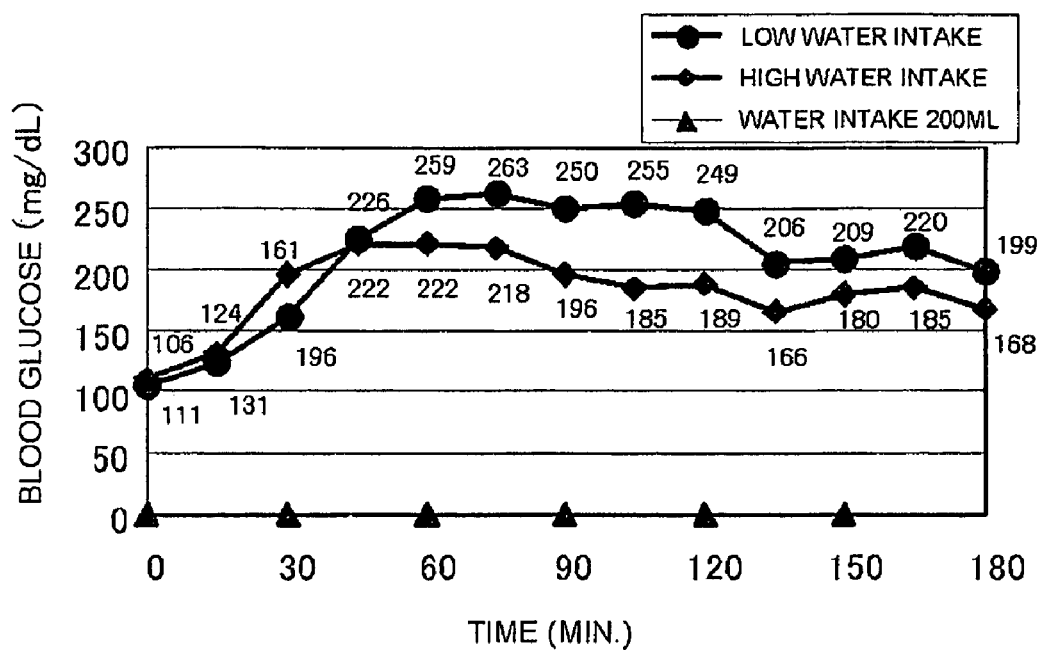
FIG. 4 is a graph showing measurement data indicating fluctuation with time of blood glucose of a subject.

FIG. 4 is a graph showing measurement data indicating fluctuation with time of the blood glucose of the subject.

Figure 5:
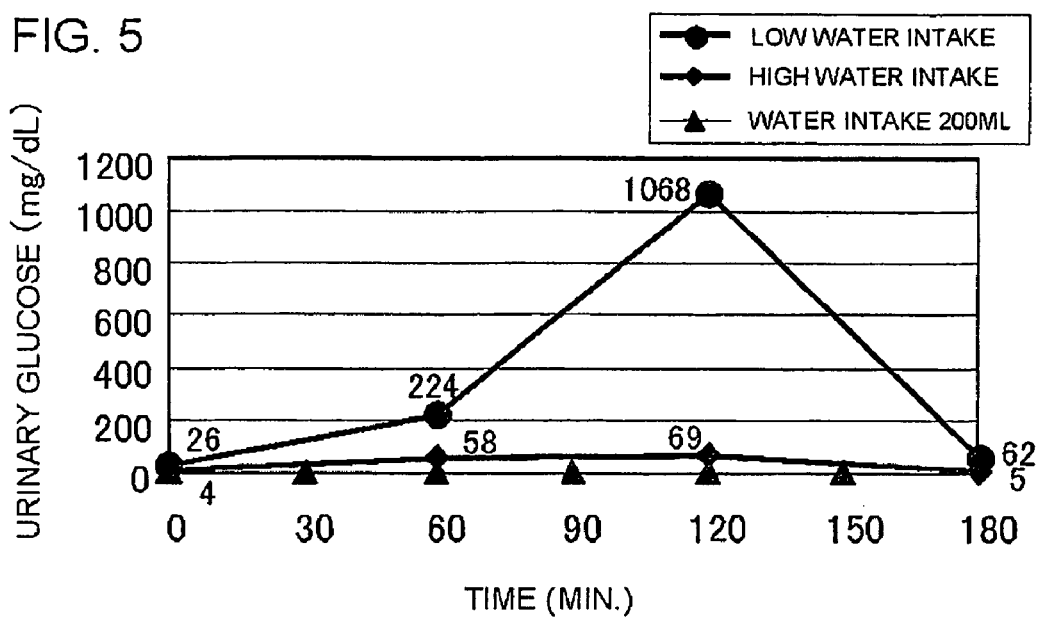
FIG. 5 is a graph showing measurement data indicating fluctuation with time of urinary glucose of the subject.

FIG. 5 is a graph showing measurement data indicating fluctuation with time of the urinary glucose of the subject.

FIG. 4 indicates that the Cases 1 and 2, in which the subject intook water at the start of the testing, showed similar tendency up to 45 minutes, however showed a visible difference after 60 minutes, where the influence of the additional water intake starts to appear. In the Case 2 with the greater water intake, the blood glucose was constantly lower by approx. 30 to 70 mg/dL after 60 minutes, than the Case 1 with the less water intake.

FIG. 5 shows a more significant difference between the Cases 1 and 2, with respect to the urinary glucose. In the Case 1 with the less water intake, the urinary glucose in the urine collected at 120 minutes reached as high as 1068 mg/dL. To be more detailed, the urinary glucose in the urine collected at 60 minutes was 224 mg/dL, and that at 180 minutes was 62 mg/dL, both of which were much lower. This indicates that the urinary glucose was predominantly excreted from the subject during the time frame of 60 to 120 minutes.

Figure 6:
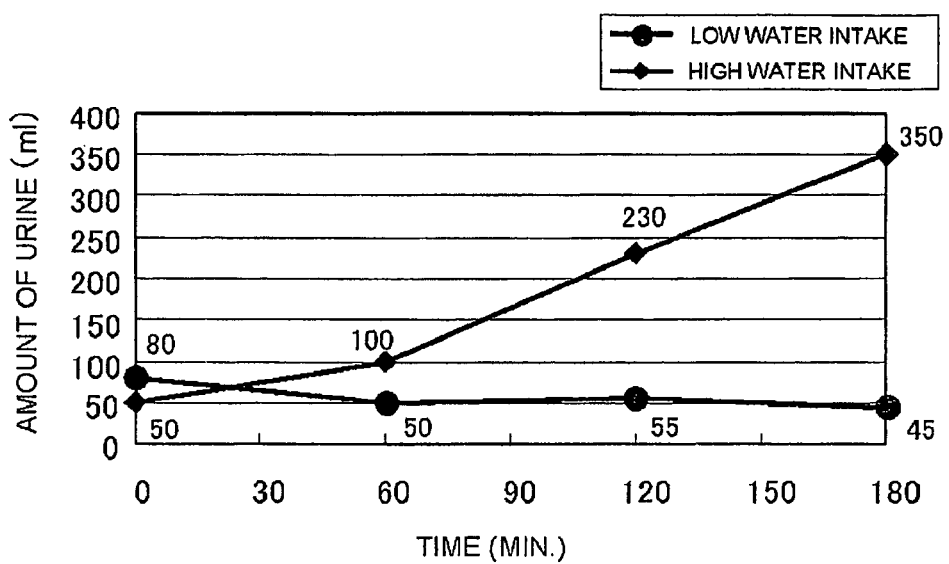
FIG. 6 is a graph showing amounts of urine collected at the start of experiment (0 minute) and every 60 minutes thereafter.

FIG. 6 is a graph showing the amounts of urine collected at the start of experiment (0 minute) and every 60 minutes thereafter. Between the Cases 1 and 2 with different water intake amounts, a significant difference in urination amount was observed, especially after 120 minutes.

Figure 7:
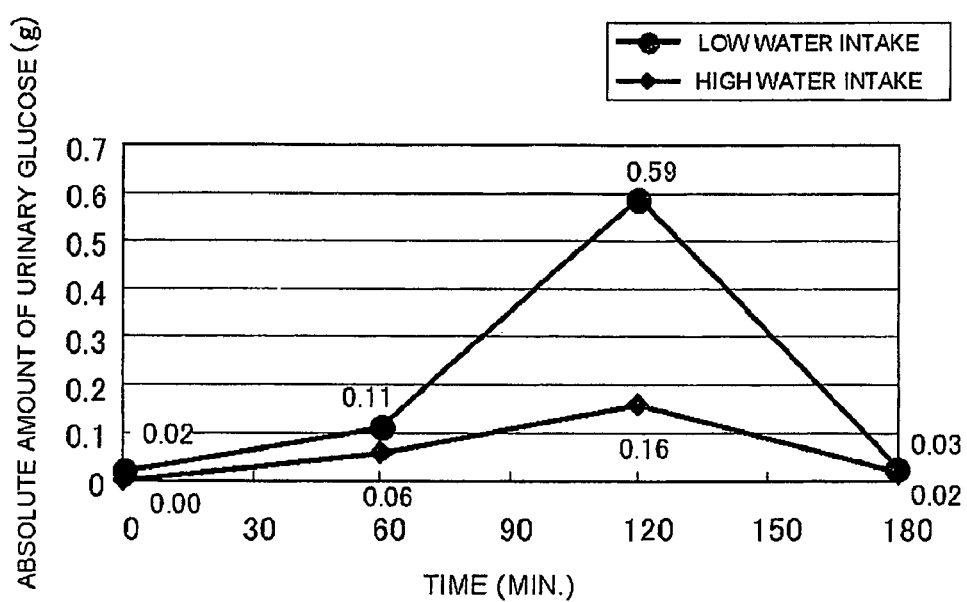
FIG. 7 is a graph showing fluctuation in absolute amount of urinary glucose, calculated from the urinary glucose and the amount of the urine.

FIG. 7 is a graph showing fluctuation in absolute amount of urinary glucose, calculated from the urinary glucose level and the amount of the collected urine. From FIG. 7, it is understood that the urinary glucose (postprandial urinary glucose) was lowered in the Case 2 with the greater water intake (Ref. FIG. 5). Based on the results of FIGS. 4, 5, and 7, it has also been proved that a reason of the decrease in urinary glucose level is not only that the urine was diluted, but that the decrease in blood glucose led to a decrease in absolute amount of the urinary glucose excreted into the urine.

Figure 8:
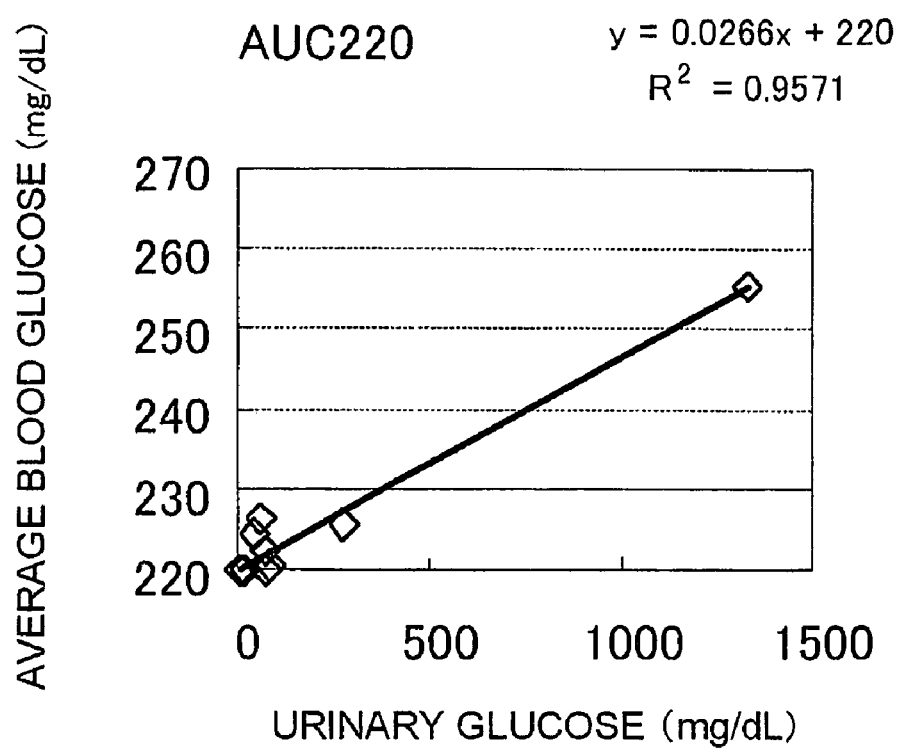
FIG. 8 is a graph showing a correlation between the urinary glucose and the average postprandial blood glucose, obtained under a renal glucose excretion threshold of 220 mg/dL.

FIG. 8 is a graph showing the correlation between the 120-minutes urinary glucose and the average postprandial blood glucose, calculated based on the results obtained from repeated experiments under the same conditions as Table 1. For FIG. 8, the average postprandial blood glucose was calculated based on the renal glucose excretion threshold of 220 mg/dL.

FIG. 8 includes plots indicating the correspondence between the urinary glucose levels at 60 minutes, 120 minutes, and 180 minutes after meal, and the average blood glucose through the elapsed time after the preceding urination (i.e. 60 minutes), with respect to each of the Cases 1 and 2. The horizontal axis is for the urinary glucose at 60 minutes, 120 minutes, and 180 minutes after meal (0-60-minutes urinary glucose, 60-120-minutes urinary glucose, and 120-180-minutes urinary glucose). The vertical axis is for the average blood glucose, calculated according to the foregoing equation (3a), based on the AUC corresponding to the time frames of 0 to 60 minutes, 60 to 120 minutes, and 120 to 180 minutes after meal under the curve created from the instantaneous blood glucose measured every 15 minutes after meal, and the elapsed time of 60 minutes.

Figure 9:
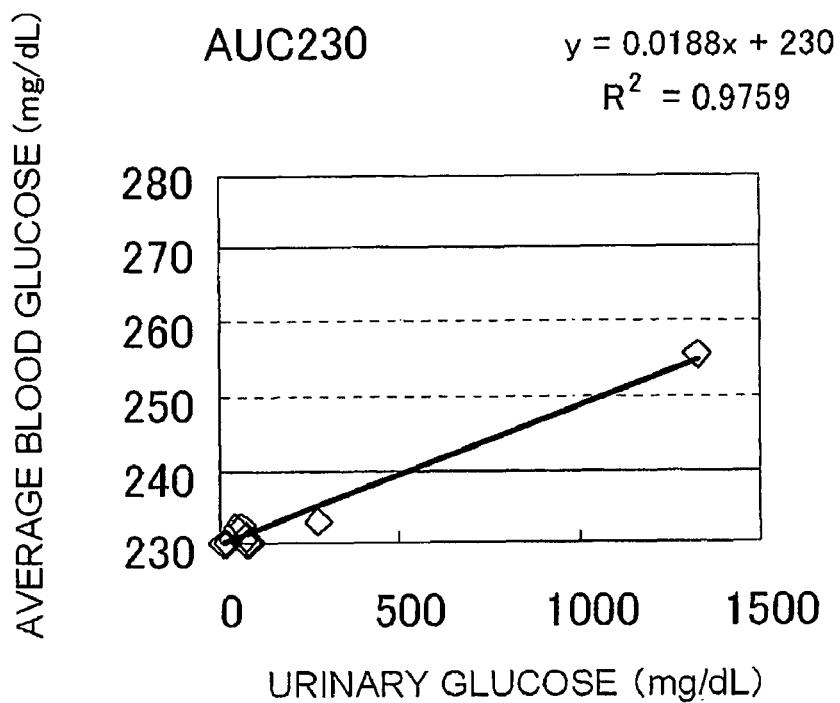
FIG. 9 is a graph showing a correlation between the urinary glucose and the average postprandial blood glucose, obtained under the renal glucose excretion threshold of 230 mg/dL.
Figure 10:
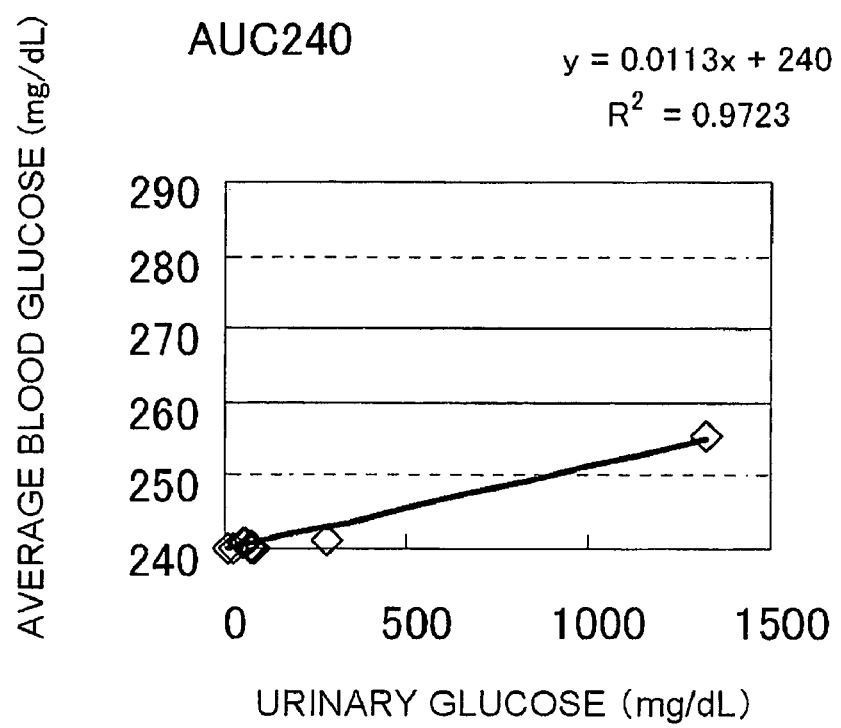
FIG. 10 is a graph showing a correlation between the urinary glucose and the average postprandial blood glucose, obtained under the renal glucose excretion threshold of 240 mg/dL.

Likewise, FIG. 9 is a graph showing the correlation in the case where the renal glucose excretion threshold was set at 230 mg/dL, and FIG. 10 at 240 mg/dL.

The coefficient of determination ($R^2$) indicating the closeness of the correlation between the postprandial urinary glucose and the average postprandial blood glucose resulted to be over 0.95, which is extremely high, in all the cases where the renal glucose excretion threshold was set at 220 to 240 mg/dL, as indicated in each drawing.

The correlation coefficient (R) resulted to be 0.978 in the case of FIG. 8, 0.988 in the case of FIG. 9, and 0.986 in the case of FIG. 10.

From the foregoing results, it has been proved that a close correlation exists between the postprandial urinary glucose and the average postprandial blood glucose, irrespective of the difference in water intake condition of the subject and in elapsed time after meal for measuring the urinary glucose. It has also been proved that the close correlation between the postprandial urinary glucose and the average postprandial blood glucose remains unchanged, under different renal excretion threshold settings.

From this working example, it has been proved that although the postprandial urinary glucose level decreases because of water intake, the increase in postprandial blood glucose is also suppressed, and that hence the correlation between the average postprandial blood glucose and the postprandial urinary glucose is not affected by the water intake condition.

Consequently, it has been proved that the average postprandial blood glucose, which is a useful index for evaluating the severity of diabetes, can be estimated based on the postprandial urinary glucose of the subject.

Working Example 2

Figure 11:
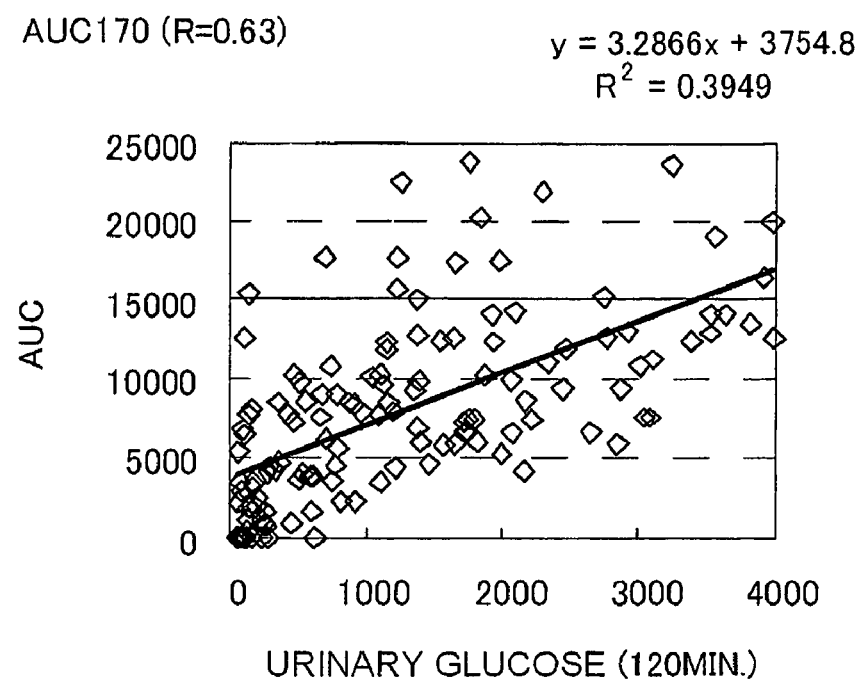
FIG. 11 is a graph including a scatter diagram of sample data showing a correlation between the 120-minutes urinary glucose and AUC of a blood glucose curve, and a regression line of the plots, obtained under the renal glucose excretion threshold of 170 mg/dL.

FIG. 11 is a graph including a scatter diagram of sample data showing a correlation between the 120-minutes urinary glucose and the AUC of the blood glucose acquired from 133 sample providers including both males and females, and a regression line (calibration line) obtained through a minimum square method. The AUC in FIG. 11 was calculated by creating the blood glucose curve based on the postprandial blood glucose acquired from the sample providers every 30 minutes after meal, as in the case of FIG. 3, and with the renal glucose excretion threshold set at 170 mg/dL.

As a result, it has been proved that the sample data containing the 120-minutes urinary glucose (x) and the AUC of the postprandial blood glucose (y) bears the correlation defined by the following equation (7):

$$y=3.3x+3.8\cdot 10^3 \tag{7}$$

In FIG. 11, the correlation coefficient (R) resulted to be as high as 0.63, which indicates that a certain correlation exists between the 120-minutes urinary glucose and the AUC of the blood glucose, with respect to a multitude of sample providers.

Thus, the calibration line defined by the equation (7) has been established, as the calibration data for estimating the AUC of the postprandial blood glucose from the 120-minutes urinary glucose.

Figure 12:
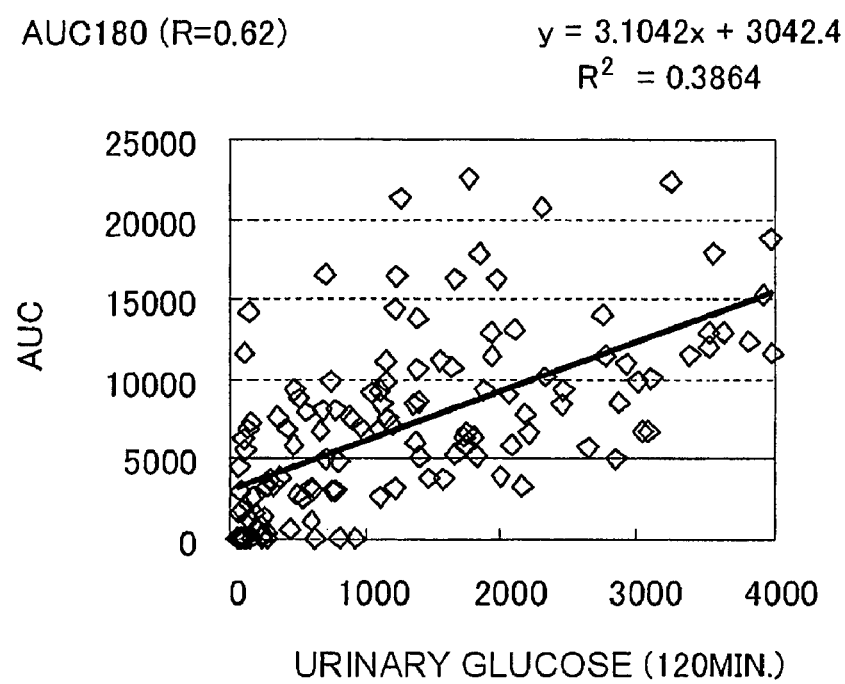
FIG. 12 is a graph including a scatter diagram of sample data and a regression line thereof, obtained under the renal glucose excretion threshold of 180 mg/dL.

FIG. 12 is a graph including a scatter diagram of sample data showing a correlation between the 120-minutes urinary glucose and the AUC calculated with the renal glucose excretion threshold set at 180 mg/dL, based on the measured data from the same sample providers, and a regression line obtained in the same way as FIG. 11.

As a result, it has been proved that the sample data containing the 120-minutes urinary glucose (x) and the AUC of the postprandial blood glucose (y) bears the correlation defined by the following equation (8):

$$y=3.1x+3.0\cdot 10^3 \tag{8}$$

Also, the correlation coefficient (R) based on the equation (8) resulted to be as high as 0.62.

Figure 13:
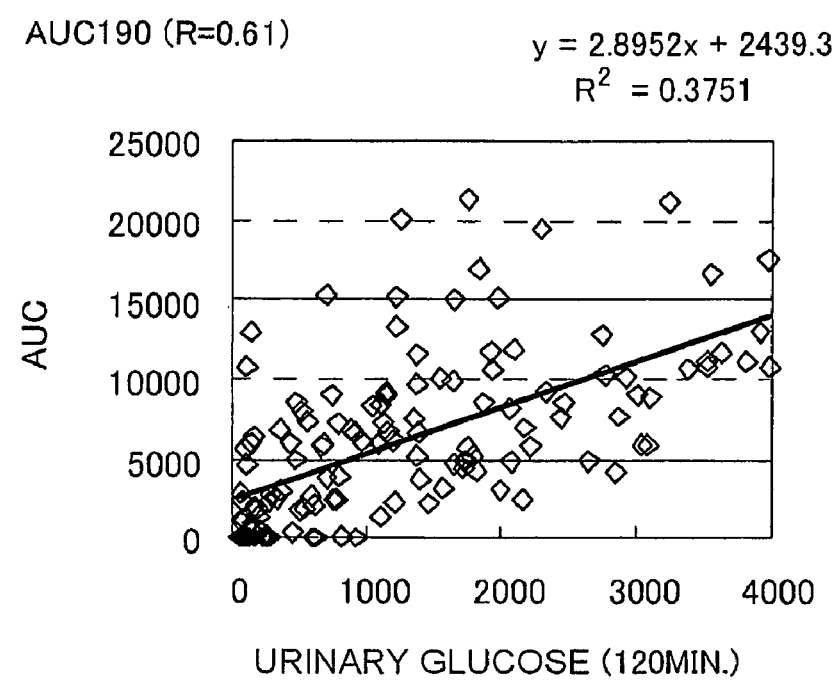
FIG. 13 is a graph including a scatter diagram of sample data and a regression line thereof, obtained under the renal glucose excretion threshold of 190 mg/dL.

FIG. 13 is a graph including a scatter diagram of sample data showing a correlation between the 120-minutes urinary glucose and the AUC calculated with the renal glucose excretion threshold set at 190 mg/dL, based on the measured data from the same sample providers, and a regression line obtained in the same way as FIG. 11.

As a result, it has been proved that the sample data containing the 120-minutes urinary glucose (x) and the AUC of the postprandial blood glucose (y) bears the correlation defined by the following equation (9):

$$y=2.9x+2.4\cdot 10^3 \tag{9}$$

Also, the correlation coefficient (R) based on the equation (9) resulted to be as high as 0.61.

From the results shown in FIGS. 11 to 13, it has been proved that a certain correlation exists between the postprandial urinary glucose and the AUC of the blood glucose, with respect to a multitude of sample providers. Accordingly, employing as the calibration data the equations (7) to (9) defining the calibration line of the sample data enables obtaining the AUC of the postprandial blood glucose of a subject, based on the 120-minutes urinary glucose of the subject.

Working Example 3

Categorizing the sample providers from different viewpoints leads to establishing a closer correlation between the postprandial urinary glucose and the average postprandial blood glucose.

In this working example, the sample providers were classified by sex.

Figure 14A:
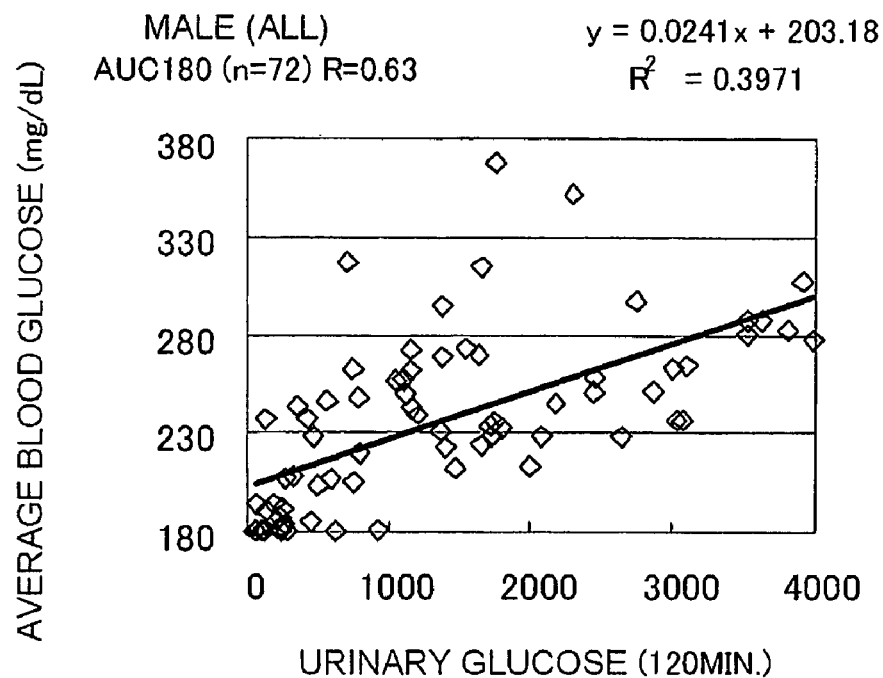
FIGS. 14A and 14B are graphs including a scatter diagram and a regression line thereof showing a correlation between the 120-minutes urinary glucose and the average postprandial blood glucose classified by sex, with respect to male sample providers and female sample providers respectively.
Figure 14B:
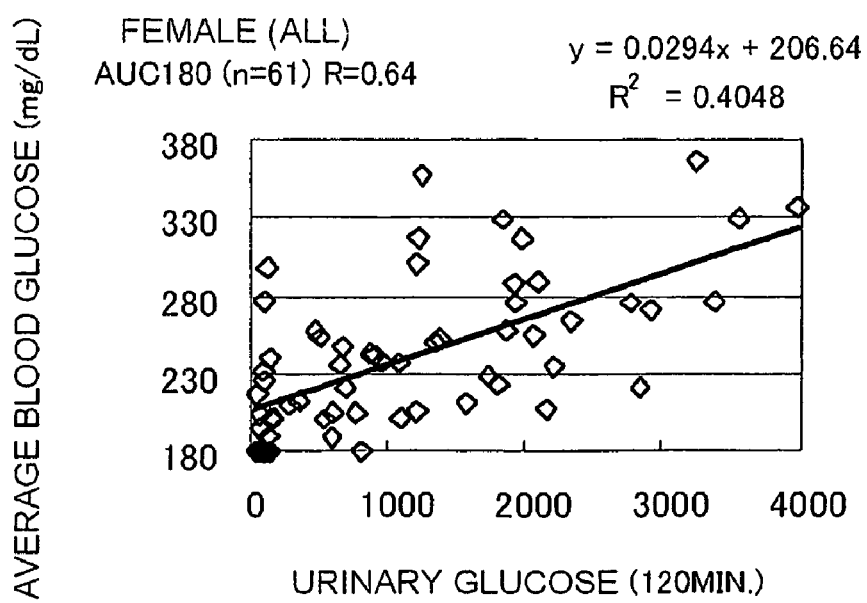

FIGS. 14A and 14B are graphs including a scatter diagram and a regression line thereof, showing a correlation between the 120-minutes urinary glucose and the average postprandial blood glucose classified by sex. FIG. 14A shows the data from the male sample providers, and FIG. 14B from the female sample providers.

In this embodiment, the average postprandial blood glucose was calculated with the following equation (10):

$$\text{Average postprandial blood glucose} = \text{renal glucose excretion threshold} + AUC \text{ of blood glucose curve} / \text{elapsed time before collection of urine after meal} \tag{10}$$

In this case, the renal glucose excretion threshold was set at 180 mg/dL, and the elapsed time before the collection of urine after meal was set at 120 minutes.

The following equation (11) has been established, as the calibration data obtained through statistically analyzing the sample data containing the 120-minutes urinary glucose and the average postprandial blood glucose acquired from 72 male sample providers:

$$\text{Average postprandial blood glucose } (y) = \text{regression coefficient} \times \text{postprandial urinary glucose } (x) + \text{threshold value} \tag{11}$$

This working example employs such threshold value that maximizes the correlation coefficient between the postprandial urinary glucose and the average postprandial blood glucose, through the minimum square method.

From the result shown in FIG. 14A, it has been proved that in the case of male sample providers the sample data containing the 120-minutes urinary glucose (x) and the postprandial blood glucose (y) bears the correlation defined by the following equation (12):

$$y=0.024x+2.0\cdot 10^2 \tag{12}$$

Thus, the regression coefficient resulted to be 0.024, and the threshold value was $2.0 \cdot 10^2$. The correlation coefficient (R) in this case resulted to be as high as 0.63.

Also, with respect to 61 female sample providers, the data was statistically analyzed in the same way as with the male sample providers, and the calibration data defined as the equation (11) was obtained. The result is shown in FIG. 14B.

Specifically, it has been proved that in the case of female sample providers the sample data containing the 120-minutes urinary glucose (x) and the postprandial blood glucose (y) bears the correlation defined by the following equation (13):

$$y=0.029x+2.1\cdot 10^2 \qquad (13)$$

Thus, the regression coefficient resulted to be 0.029, and the threshold value was $2.1 \cdot 10^2$. The correlation coefficient (R) in this case resulted to be as high as 0.64.

Working Example 4

The sample providers were categorized by sex and HbA1c concentration, and the calibration data of the correlation between the 120-minutes urinary glucose and the average postprandial blood glucose was calculated, as in the case of the working example 2.

Figure 15A:
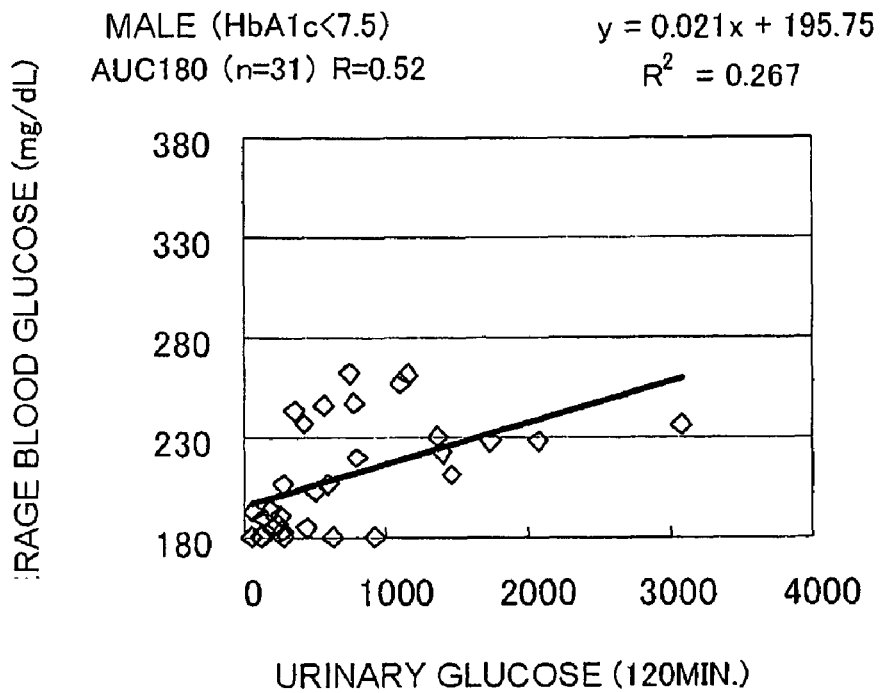
FIGS. 15A and 15B are graphs including a scatter diagram and a regression line thereof showing a correlation between the 120-minutes urinary glucose and the average postprandial blood glucose classified by sex and HbA1c concentration, with respect to male sample providers and female sample providers respectively.

FIG. 15A includes a scatter diagram based on the sample data from 31 male sample providers having the HbA1c lower than 7.5%.

The calibration line for the 120-minutes urinary glucose (x) and the average postprandial blood glucose (y), obtained through the minimum square method from such sample data, was defined by the following equation (14), and the correlation coefficient (R) resulted to be 0.52:

$$y=0.021x+2.0\cdot 10^2 \qquad (14)$$

Figure 15B:
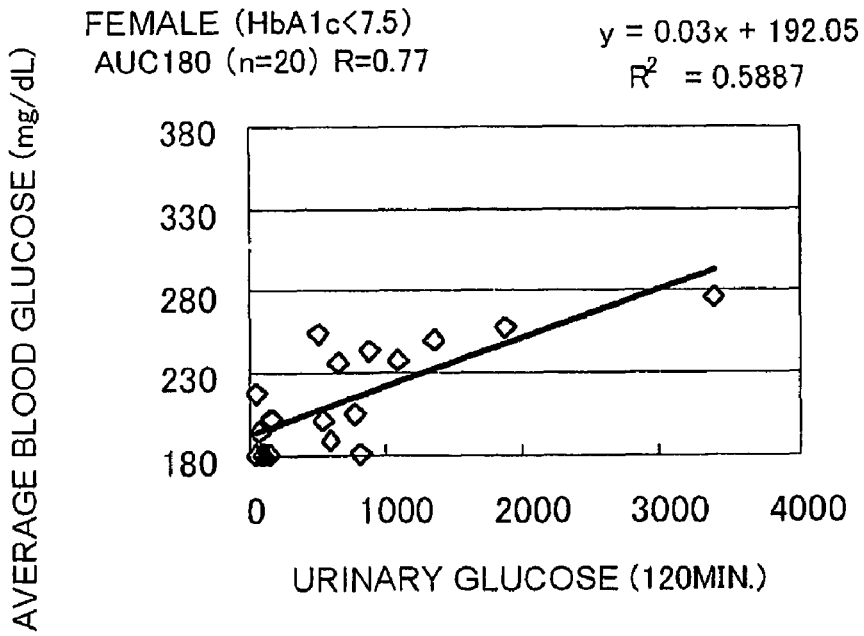

FIG. 15B includes a scatter diagram based on the sample data from 20 female sample providers having the HbA1c lower than 7.5%.

The calibration line for the 120-minutes urinary glucose (x) and the average postprandial blood glucose (y), obtained through the minimum square method from such sample data, was defined by the following equation (15), and the correlation coefficient (R) resulted to be as high as 0.77:

$$y=0.030x+1.9\cdot 10^2 \qquad (15)$$

Figure 16A:
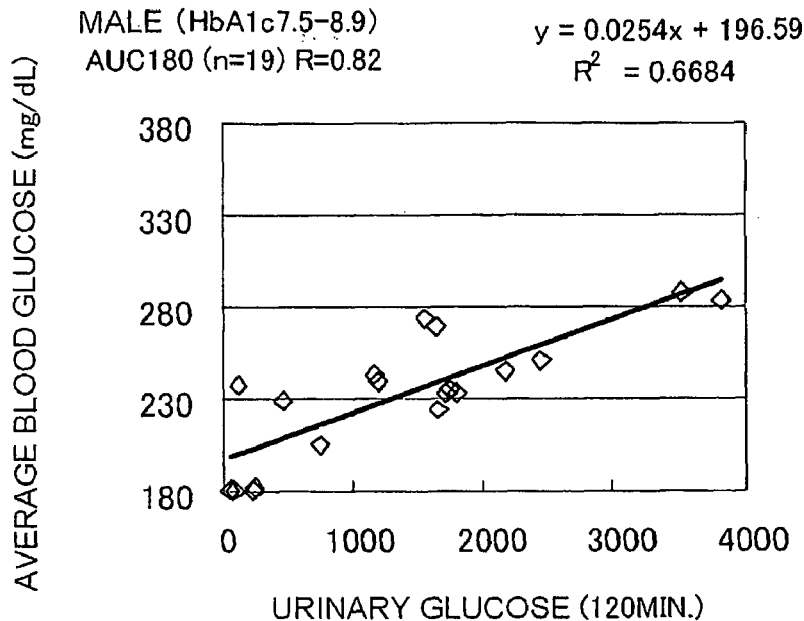
FIGS. 16A and 16B are graphs including a scatter diagram and a regression line thereof showing a correlation between the 120-minutes urinary glucose and the average postprandial blood glucose classified by sex and HbA1c concentration, with respect to male sample providers and female sample providers respectively.

FIG. 16A includes a scatter diagram based on the sample data from 19 male sample providers having the HbA1c within a range of 7.5% to 8.9%.

The calibration line for the 120-minutes urinary glucose (x) and the average postprandial blood glucose (y), obtained through the minimum square method from such sample data, was defined by the following equation (16), and the correlation coefficient (R) resulted to be 0.82, which is quite high:

$$y=0.025x+2.0\cdot 102 \qquad (16)$$

Figure 16B:
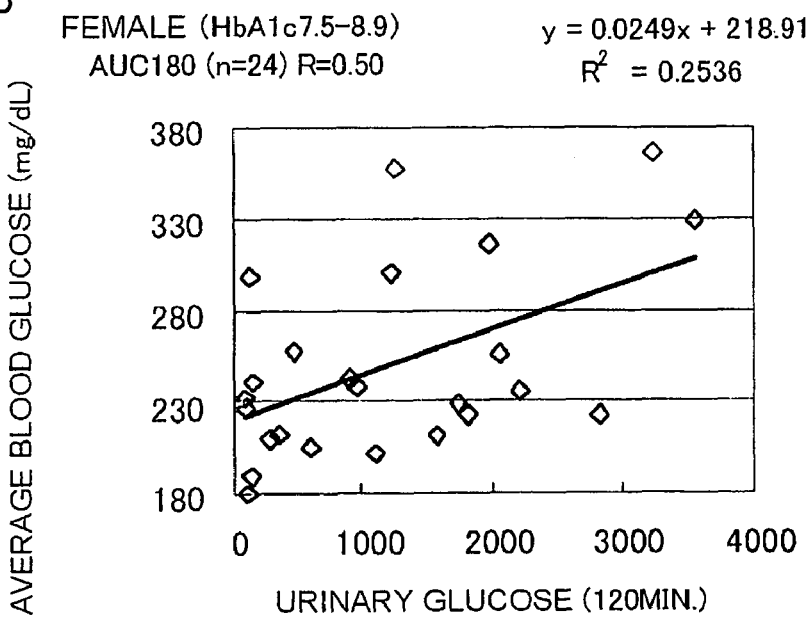

FIG. 16B includes a scatter diagram based on the sample data from 24 female sample providers having the HbA1c within a range of 7.5% to 8.9%.

The calibration line for the 120-minutes urinary glucose (x) and the average postprandial blood glucose (y), obtained through the minimum square method from such sample data, was defined by the following equation (17), and the correlation coefficient (R) resulted to be 0.50:

$$y=0.025x+2.2\cdot 10^2 \qquad (17)$$

Figure 17A:
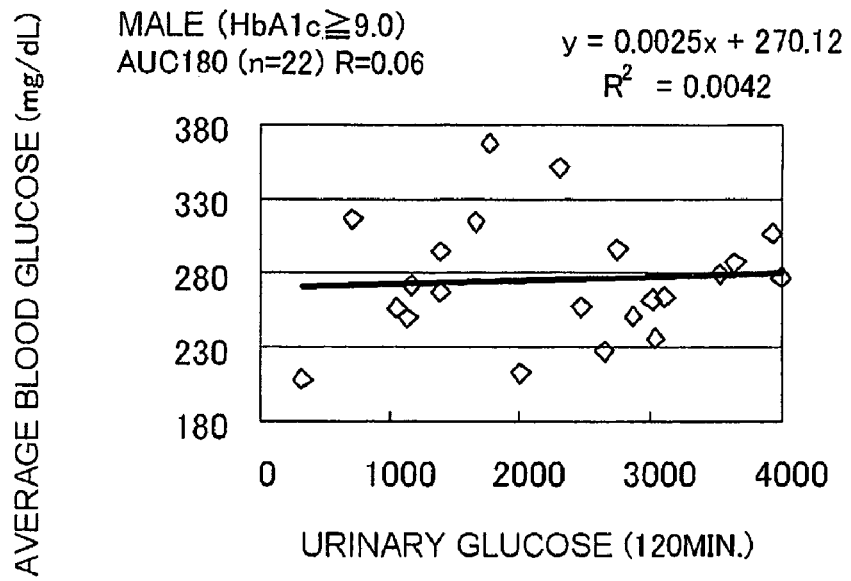
FIGS. 17A and 17B are graphs including a scatter diagram and a regression line thereof showing a correlation between the 120-minutes urinary glucose and the average postprandial blood glucose classified by sex and HbA1c concentration, with respect to male sample providers and female sample providers respectively.

FIG. 17A includes a scatter diagram based on the sample data from 22 male sample providers having the HbA1c not lower than 9.0%.

The calibration line for the 120-minutes urinary glucose (x) and the average postprandial blood glucose (y), obtained through the minimum square method from such sample data, was defined by the following equation (18), and the correlation coefficient (R) resulted to be as low as 0.06:

$$y=0.0025x+2.7\cdot 10^2 \qquad (18)$$

Figure 17B:
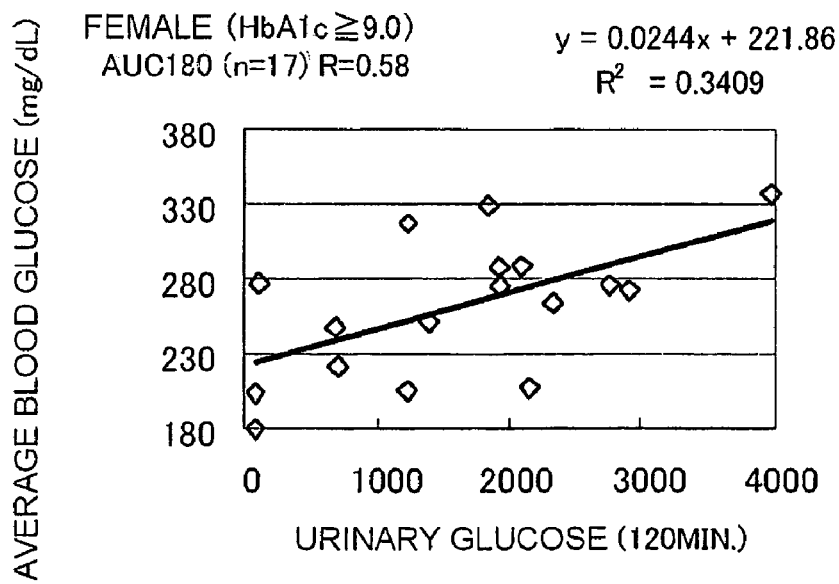

FIG. 17B includes a scatter diagram based on the sample data from 17 female sample providers having the HbA1c not lower than 9.0%.

The calibration line for the 120-minutes urinary glucose (x) and the average postprandial blood glucose (y), obtained through the minimum square method from such sample data, was defined by the following equation (19), and the correlation coefficient (R) resulted to be 0.58:

$$y=0.0024x+2.2\cdot 10^2 \qquad (19)$$

From the foregoing results, it has been proved through this working example that a particularly close correlation was observed between the postprandial urinary glucose and the average postprandial blood glucose, in the case of the male sample providers having the HbA1c concentration lower than 9.0%, and the female sample providers having the HbA1c concentration lower than 7.5%. Consequently, it is understood that the method according to the present invention is capable of measuring the average postprandial blood glucose of such subjects with particularly high estimation accuracy.

Working Example 5

The sample providers of the same sex and HbA1c concentration were classified into two groups, and the calibration data for the 120-minutes urinary glucose and the average postprandial blood glucose was calculated from the respective groups.

Figure 18A:
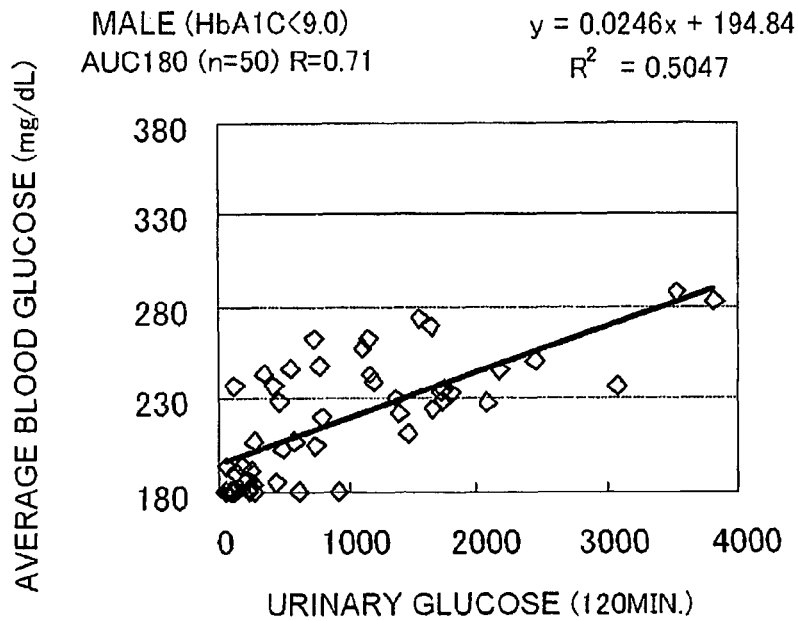
FIGS. 18A and 18B are graphs including a scatter diagram and a regression line thereof with respect to male sample providers having HbA1c lower than 9.0%, taken as a single group and as two groups respectively.

FIG. 18A is a graph containing the data of FIGS. 15A and 16A. In other words, FIG. 18A includes a scatter diagram and a regression line (calibration line) thereof, of the sample data of the 120-minutes urinary glucose (x) and the average postprandial blood glucose (y) from 50 male sample providers having the HbA1c lower than 9.0%. FIG. 18A shows the result of statistically analyzing the data of those male sample providers taken as one group.

Such calibration line is defined by the following equation (20), and the correlation coefficient (R) resulted to be 0.71, which is relatively high:

$$Y=0.025x+1.9\cdot 10^2 \qquad (20)$$

Figure 18B:
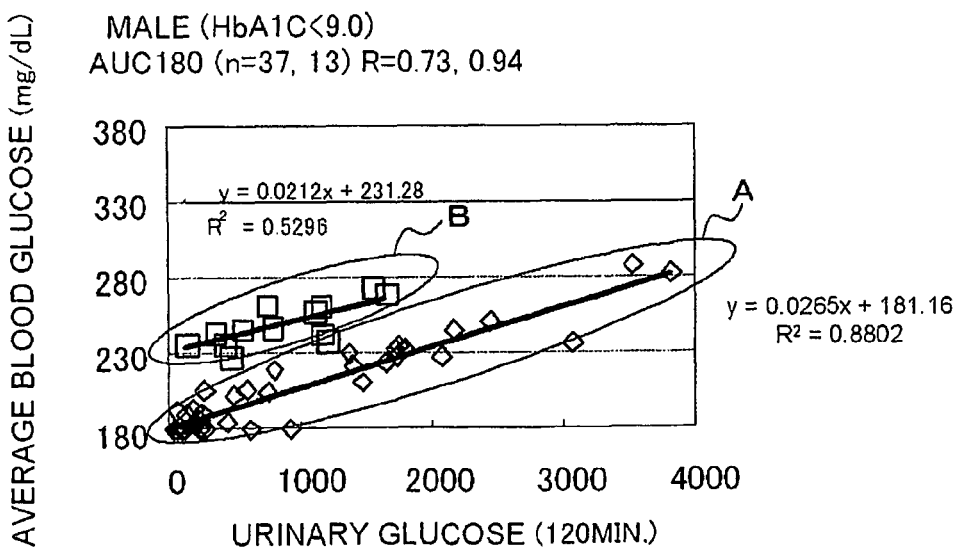

FIG. 18B shows the calibration line obtained with respect to each group formed by classifying the sample data of those 50 male sample providers into two groups. From the scatter diagram shown therein, it is understood that the 50 male sample providers having the HbA1c lower than 9.0% were classified into a group (A) of 37 persons showing lower average postprandial blood glucose levels and the other group (B) of 13 persons showing higher average postprandial blood glucose levels, with respect to the same 120-minutes urinary glucose level.

Accordingly, the sample providers were categorized into a plurality of groups based on the conversion ratio, which represents the level of the average postprandial blood glucose with respect to a given postprandial urinary glucose, and the calibration data indicating the correlation between the postprandial urinary glucose and the average postprandial blood glucose was calculated, with respect to each group.

As a result, the following equation (21) has been established with respect to the group (A):

$$y=0.027x+1.8 \cdot 10^2 \quad (21)$$

With respect to the group (B), the calibration data defined by the following equation (22) has been obtained:

$$y=0.021x+2.3 \cdot 10^2 \quad (22)$$

The correlation coefficient of the group (A) resulted to be 0.94 and that of the group (B) 0.73, both of which are excellent values.

This working example has thus proved to be suitably applicable, from FIG. 18B, to the male sample providers and a male subject having the HbA1c concentration lower than 9.0%.

In the case where the sample providers are female, or where the HbA1c concentration is in a different range, the respective categories may further be classified into a plurality of groups, according to the conversion ratio of the average postprandial blood glucose with respect to the postprandial urinary glucose.

The results of this working example indicates that classifying the correlation data acquired in the sample acquisition process into a plurality of groups, and obtaining in advance the calibration data of each group, enables associating the postprandial urinary glucose and the average postprandial blood glucose under a high correlation coefficient.

Consequently, recognizing once to which group the subject belongs enables estimating, in the subsequent measurement, the average postprandial blood glucose with higher accuracy, employing the calibration data corresponding to the group to which the subject belongs.

Combining the results of the working example 1 and those of the working examples 2 to 5 enables estimating the average postprandial blood glucose from the measured value of the postprandial urinary glucose, irrespective of the water intake or perspiration of the subject.

Specifically, it has been proved from the working example 1 that the postprandial urinary glucose (x) and the average postprandial blood glucose (y), under different water intake conditions as shown in FIGS. 8 to 10, can be mutually associated with an extremely high correlation coefficient, in a similar pattern to the equation (4) regarding the sample data:

Average postprandial blood glucose (y)=regression coefficient×postprandial urinary glucose (x)+ threshold value (4)

It has also been proved from the results of the working example 4 that the average postprandial blood glucose (mg/dL) of a subject can be quite accurately estimated, with the equation (5) in the case of a male having the HbA1c concentration lower than 9.0%, and the equation (6) in the case of a female having HbA1c concentration lower than 7.5%.

Consequently, it has been proved that the measuring device and the measurement method according to this working example enable estimating the average postprandial blood glucose of a subject irrespective of the water intake condition, through classifying the sample providers into various categories as exemplified in the working examples 2 to 5 and calculating the calibration data that associates the postprandial urinary glucose and the average postprandial blood glucose under a high correlation coefficient.

It is apparent that the present invention is not limited to the above embodiment, and may be modified and changed without departing from the scope and spirit of the invention.

What is claimed is:

1. A blood glucose measuring device, comprising:
   a storing unit that stores calibration data indicating a correlation between a postprandial urinary glucose at a predetermined time after meal and a time-averaged postprandial blood glucose through a period up to said predetermined time after meal;
   a measuring unit that measures postprandial urinary glucose from urine of a subject at said predetermined time after meal;
   a processing unit that calculates said time-averaged postprandial blood glucose, based on said postprandial urinary glucose measured; and an output unit that outputs data indicating said postprandial blood glucose calculated,
   wherein said correlation between said postprandial urinary glucose and said time-averaged postprandial blood glucose is maintained in a case where water intake or excretion takes place in said subject through drinking water or perspiration.

2. The blood glucose measuring device according to claim 1,
   wherein said measuring unit accepts said urine of said subject who has intaken water or perspired in said period up to said predetermined time after meal, to thereby measure said postprandial urinary glucose.

3. The blood glucose measuring device according to claim 2,
   wherein said processing unit calculates said time-averaged postprandial blood glucose based on said postprandial urinary glucose measured from said urine of said subject who has intaken water or perspired in said period up to said predetermined time after meal, and said postprandial urinary glucose measured from said urine of said subject who has neither intaken water nor perspired in said period up to said predetermined time after meal, utilizing said calibration data in common.

4. The blood glucose measuring device according to claim 1, further comprising an input unit that accepts an input of ratio information indicating a level of a conversion ratio from said postprandial urinary glucose to said time-averaged postprandial blood glucose of said subject;
   wherein said processing unit calculates said time-averaged postprandial blood glucose based on said postprandial urinary glucose measured, and said ratio information.

5. The blood glucose measuring device according to claim 4,
   wherein said input unit accepts an input of said ratio information selected from a first and a second of said conversion ratios, and
   the time-averaged postprandial blood glucose calculated with respect to a given said postprandial urinary glucose by application of the first conversion ratio is lower than said time-averaged postprandial blood glucose calculated with respect to said given postprandial urinary glucose by application of the second conversion ratio.

6. The blood glucose measuring device according to claim 1, further comprising an input unit that accepts an input of at least one of sex information indicating a sex of said subject, blood information indicating hemoglobin A1c concentration of said subject, and ratio information indicating a level of a conversion ratio from said postprandial urinary glucose to said time-averaged postprandial blood glucose of said subject;
   wherein said processing unit calculates said time-averaged postprandial blood glucose based on said postprandial urinary glucose measured, and at least one of said sex information, said blood information and said ratio information.

7. A method of measuring average postprandial blood glucose, comprising:
- acquiring calibration data indicating a correlation between a postprandial urinary glucose at a predetermined time after meal and a time-averaged postprandial blood glucose through a period up to said predetermined time after meal, from a plurality of sample providers;
- measuring said postprandial urinary glucose from urine of a subject at said predetermined time after meal; and
- estimating, using a processing unit, said time-averaged postprandial blood glucose of said subject based on said postprandial urinary glucose measured and said calibration data,
- wherein said correlation between said postprandial urinary glucose and said time-averaged postprandial blood glucose is maintained in a case where water intake or excretion takes place in said subject through drinking water or perspiration.

8. The method according to claim 7,
wherein said acquiring calibration data includes acquiring sample data from each of said sample providers indicating a correlation between an area of a region under a curve of a postprandial blood glucose but upper than a predetermined renal glucose excretion threshold and said postprandial urinary glucose, and statistically analyzing a plurality of said sample data acquired, to thereby calculate said calibration data.

9. The method according to claim 8,
wherein said calibration data calculated through statistical analysis forms a calibration line defined by an equation (1):

$$\text{Time-averaged postprandial blood glucose} = \text{regression coefficient} \times \text{postprandial urinary glucose} + \text{threshold value} \quad (1).$$

10. The method according to claim 9,
wherein said renal glucose excretion threshold is adopted as said threshold value and said regression coefficient is specified as $2 \times 10^{-2}$, in the case where said subject is a male and has a hemoglobin A1c concentration lower than 9.0%, and
said renal glucose excretion threshold is adopted as said threshold value and said regression coefficient is specified as $3 \times 10^{-2}$, in the case where said subject is a female and has a hemoglobin A1c concentration lower than 7.5%.

11. The method according to claim 8, in which said acquiring calibration data includes classifying said sample data acquired from said sample providers into a plurality of groups, and calculating said calibration data based on said sample data of the respective groups, further comprising:
- acquiring said sample data of said subject in advance;
- wherein said estimating said time-averaged postprandial blood glucose includes identifying one of said groups to which said sample data acquired of said subject belongs, and estimating said time-averaged postprandial blood glucose of said subject based on said calibration data corresponding to said group identified and said postprandial urinary glucose measured.

12. The method according to claim 11,
wherein said sample providers and said subject include a male having a hemoglobin A1c concentration lower than 9.0%.

13. The method according to claim 7,
further comprising accepting said urine of said subject who has intaken water or perspired in said period up to said predetermined time after meal, and measuring said postprandial urinary glucose from said urine.

14. The method according to claim 13,
wherein said estimating said time-averaged postprandial blood glucose is based on
said postprandial urinary glucose measured from said urine of said subject who has intaken water or perspired in said period up to said predetermined time after meal, and
said postprandial urinary glucose measured from said urine of said subject who has neither intaken water nor perspired in said period up to said predetermined time after meal,
utilizing said calibration data in common.

* * * * *